United States Patent
Gal-Mor et al.

(10) Patent No.: US 11,077,123 B2
(45) Date of Patent: Aug. 3, 2021

(54) USE OF BILE ACIDS AND BILE SALTS AS ANTI BACTERIAL AGENTS FOR INHIBITION OF BACTERIAL CONJUGATION AND HORIZONTAL GENE TRANSFER

(71) Applicant: Tel HaShomer Medical Research Infrastructure and Services Ltd., Ramat-Gan (IL)

(72) Inventors: Ohad Gal-Mor, Hod-HaSharon (IL); Galia Rahav, Jerusalem (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 16/080,672

(22) PCT Filed: Feb. 28, 2017

(86) PCT No.: PCT/IL2017/050254
§ 371 (c)(1),
(2) Date: Aug. 29, 2018

(87) PCT Pub. No.: WO2017/149536
PCT Pub. Date: Sep. 8, 2017

(65) Prior Publication Data
US 2019/0070200 A1    Mar. 7, 2019

Related U.S. Application Data

(60) Provisional application No. 62/300,978, filed on Feb. 29, 2016.

(51) Int. Cl.
| | |
|---|---|
| A61K 31/575 | (2006.01) |
| C02F 1/78 | (2006.01) |
| A61L 2/00 | (2006.01) |
| A61P 31/04 | (2006.01) |
| A61K 45/06 | (2006.01) |
| A61K 31/185 | (2006.01) |
| C02F 1/50 | (2006.01) |
| C02F 1/76 | (2006.01) |

(52) U.S. Cl.
CPC .......... *A61K 31/575* (2013.01); *A61K 31/185* (2013.01); *A61K 45/06* (2013.01); *A61L 2/00* (2013.01); *A61P 31/04* (2018.01); *C02F 1/50* (2013.01); *C02F 1/76* (2013.01); *C02F 1/78* (2013.01); *C02F 2303/04* (2013.01); *C02F 2303/20* (2013.01)

(58) Field of Classification Search
None
See application file for complete search history.

(56) References Cited

U.S. PATENT DOCUMENTS

| | | | | |
|---|---|---|---|---|
| 7,166,299 | B2* | 1/2007 | Yoo | A61K 9/0014 424/424 |
| 2012/0196887 | A1* | 8/2012 | Darkoh | A61K 9/1075 514/279 |

FOREIGN PATENT DOCUMENTS

| | | |
|---|---|---|
| CN | 101862311 | 10/2010 |
| WO | WO 2015/076788 | 5/2015 |
| WO | WO 2017/149536 | 9/2017 |

OTHER PUBLICATIONS

He et al (Journal of Microbiology, 2014, 52(8), 716-719). (Year: 2014).*
Conjugal Transfer of the Salmonella enterica Virulence Plasmid in the Mouse Intestine; Meritxell Garcia-Quintanilla, Journal of Bacteriology, Mar. 2008, p. 1922-1927, vol. 190, No. 6 (Year: 2008).*
International Preliminary Report on Patentability dated Sep. 13, 2018 From the International Bureau of WIPO Re. Application No. PCT/IL2017/050254. (9 Pages).
International Search Report and the Written Opinion dated May 28, 2017 From the International Searching Authority Re. Application No. PCT/IL2017/050254. (15 Pages).
Anderson "Factors That May Prevent Transfer of Antibiotic Resistance Between Gram-Negative Bacteria in the Gut", Journal of Medical Microbiology, 8(1): 83-88, Feb. 1975. 'Factors Affecting R-Factor Transfer', p. 84-85, Table, p. 85, Last Para.
Cabezon et al. "Towards an Integrated Model of Bacterial Conjugation", FEMS Microbiology Reviews, 39(1): 81-95, Published Online Dec. 14, 2014.
Elkins et al. "Bile-Mediated Aminoglycoside Sensitivity in Lactobacillus Species Likely Results From Increased Membrane Permeability Attributable to Cholic Acid", Applied and Environmental Microbiology, 70(12): 7200-7209, Dec. 2004. p. 7201, Left Col., 2nd Para, p. 7202, Right Col., 2nd Para, p. 7202, Right Col., Last Para—p. 7204, Right Col., 1st Para, Tables 2 & 3, Fig.1.

(Continued)

*Primary Examiner* — Celeste A Roney

(57) ABSTRACT

Methods of inhibiting bacterial conjugation, bacterial horizontal gene transfer or bacterial growth are disclosed. The methods comprise contacting bacteria with an effective amount of a bile acid or a bile salt, wherein the effective amount does not affect viability of the bacteria. A method of increasing susceptibility of bacteria to antibiotic treatment is also disclosed as well as methods of decontaminating a farm animal housing or a medical surface and methods of treating water. Also disclosed are compositions effective in inhibiting bacterial conjugation, bacterial horizontal gene transfer and bacterial growth.

30 Claims, 5 Drawing Sheets
(1 of 5 Drawing Sheet(s) Filed in Color)

(56) References Cited

OTHER PUBLICATIONS

Kishinaka et al. "High Concentration of Conjugated Bile Acids Inhibit Bacterial Growth of Clostridium Perfringens and Induce its Extracellular Cholylglycine Hydrolase", Steroids, 59(8): 485-489, Aug. 1994.
Nathan "Antibiotics at the Crossroads. Are We Making the Right Choices to Bring New Drugs to the Marketplace?", Nature, 431(7011): 899-902, Oct. 21, 2004.
Perry et al. "The Antibiotic Resistome: What's New?", Current Opinion in Microbiology, 21: 45-50, Available Online Sep. 30, 2014.
Ruiz et al. "Bile Resistance Mechanisms in Lactobacillus and Bifidobacterium", Frontiers in Microbiology, 4(Art.396): 1-8, Dec. 24, 2013.
Sung et al. "Anibacterial Activity of Bile Salts Against Common Biliary Pathogens", Digestive Diseases and Sciences, 38(11): 2104-2112, Nov. 15, 1993 Abstract, Figs.1a, 4, p. 2111, Right Col., First Para.
Van den Bogaard et al. "Antibiotic Resistance of Faecal *Escherichia coli* in Poultry, Poultry Farmers and Poultry Slaughterers", Journal of Antimicrobial Chemotherapy, 47(6): 763-771, Jun. 2001.
Supplementary Partial European Search Report and the European Provisional Opinion dated Sep. 30, 2019 From the European Patent Office Re. Application No. 17759380.3. (17 Pages).
Aviv et al. "Horizontal Transfer of the Salmonella Enterica Serovar Infantis Resistance and Virulence Plasmid pEST to the Gut Microbiota of Warm-Blooded Hosts", mBio, American Society for Microbiology, XP055623713, 7(5): e0139516-1-e01395-16-12, Published Online Sep. 6, 2016.
Watanabe "Infective Heredity of Multiple Drug Resistance in Bacteria", Bacteriology Review, XP055623892, 27(1): 87-115, Mar. 1, 1963.
Supplementary European Search Report and the European Search Opinion dated Feb. 12, 2020 From the European Patent Office Re. Application No. 17759380.3. (30 Pages).
Sorg et al. "Chenodeoxycholate is an Inhibitor of Clostridium Difficile Spore Germination", Journal of Bacteriology, XP055027727, 191(3): 1115-1117, Feb. 1, 2009.

\* cited by examiner

USE OF BILE ACIDS AND BILE SALTS AS ANTI BACTERIAL AGENTS FOR INHIBITION OF BACTERIAL CONJUGATION AND HORIZONTAL GENE TRANSFER

RELATED APPLICATIONS

This application is a National Phase of PCT Patent Application No. PCT/IL2017/050254 having International filing date of Feb. 28, 2017, which claims the benefit of priority under 35 USC § 119(e) of U.S. Provisional Patent Application No. 62/300,978 filed on Feb. 29, 2016. The contents of the above applications are all incorporated by reference as if fully set forth herein in their entirety.

FIELD AND BACKGROUND OF THE INVENTION

The present invention, in some embodiments thereof, relates to bile acids and bile salts or compositions comprising same and, more particularly, but not exclusively, to the use of same for inhibition of bacterial conjugation or bacterial horizontal gene transfer, and further for disruption of acquisition of antibiotic resistance.

Antimicrobial resistance of bacteria is one of the most difficult challenges of the modern medicine. In September 2013 the Centers for Disease Control and Prevention (CDC) issued a threat report, naming infections with *Clostridium difficile*, Carbapenem-resistant Enterobacteriaceae (CRE), and drug-resistant *Neisseria gonorrhoeae* as among the most urgent medical problems (Antibiotic Resistance Threats in the United States, 2013: Centers for Disease Control and Prevention. Sep. 16, 2013).

The initial rate of bacterial resistance to new drugs is normally about 1%. However, modern usage of antibiotics has caused a massive increase in the number of resistant bacteria. Studies show that within 8-12 years after ubiquitous usage, strains resistant to multiple drugs become widespread. Multiple drug resistant strains of some bacteria have reached the proportion that virtually no antibiotics are available for treatment and their natural phenotype is multidrugs resistant [Nathan C., Nature (2004) 431(7011): 899-902].

While pathogens have become multi-drug or extensively drug resistant, drug companies are dramatically reducing their drug discovery programs resulting in severe public health consequences and lack of suitable antibiotic therapy [Perry J. A. et al., Current opinion in microbiology (2014) 21: 45-50]. Today, it is clear that combating the problem requires an understanding of the biological principles and factors that lead to the evolution, divergence, and spread of antimicrobial resistance (AMR) genes.

Several bacterial mechanisms have evolved in order to acquire resistance to antibiotics. These mechanisms involve modification of existing genetic material or the acquisition of new genetic material from another source. The main mechanism is the acquisition of AMR genes by bacterial conjugation via plasmid transfer. This is a process by which genetic material is transferred from a donor cell to a recipient cell. The transfer of these conjugative genes requires sophisticated machinery that ensures DNA mobilization and mating pair formation. These genes can be encoded by an autonomous replicating plasmid or by integrative conjugative elements (ICE) inserted in the bacteria chromosome. Conjugation in Gram-negative bacteria is mediated by transfer of conjugative plasmids through a designated tube-like structure (a pilus, which represents a subset of the type four secretion system family) from a donor bacterium to a recipient cell that can be a distantly related species [Cabezon E. et al., FEMS microbiology reviews (2015) 39(1): 81-95].

Antimicrobial resistance of bacteria is also a prominent problem in agriculture settings, such as in dairy, poultry and turkey farms. In farm animals, antimicrobial agents are used for therapy and prevention of bacterial infections as well as for growth promotion. Bacterial infections in poultry include *Escherichia coli* (*E. Coli*), *Salmonella enterica* (*S. enterica*), *Enterococcus faecalis* as well as other pathogens. The control of these infections is imperative as *S. enterica*, for example, can colonize in a chicken's intestinal tract without necessarily causing obvious disease symptoms in the chicken. However, the bacteria (including resistant strains) may invade other chicken tissues and can eventually find its way into the reproductive tract and ovary, leading to laying of contaminated eggs. Likewise, at slaughter, bacterial strains from the gut, such as *E. coli* and *Salmonella*, readily soil poultry carcasses and as a result poultry meats may be contaminated with bacteria, including resistant bacterial strains [van der Bogaard, J. Antimicrob. Chemother. (2001) 47(6): 763-771]. Therapy with antibiotics significantly increases the risk for generating bacterial resistant strains in both humans and animals.

Bile salts, the main components of bile, are detergent-like biological substances synthesized in the liver from cholesterol. Bile salts are stored in the gall bladder and are released into the duodenum during digestion to perform their physiological function, i.e. the solubilization of fat coming from diet. Bile salts also possess a strong antimicrobial activity, as they are able to disorganize the structure of the cell membrane, as well as trigger DNA damage. Therefore, bacteria inhibiting the intestinal tract must have intrinsic resistance mechanisms to cope with bile salts. Thus, intestinal bacteria, such as *Lactobacillus* and *Bifidobacterium*, display a variety of proteins devoted to the efflux of bile salts or protons, to modify sugar metabolism or to prevent protein misfolding [Ruiz et al., Frontiers in Microbiology (2013) Volume 4: 396]. Other highly ubiquitous enteropathogens such as *E. coli, Shigella*, and *Salmonella* are resistant to bile.

According to Kishinaka et al. [Steroids. (1994) 59(8):485-9], exposure of *Clostridium perfringens*, a spore-forming gram-positive bacterium found in raw meat and poultry, as well as in the intestines of humans and animals, to varying concentrations of taurine- or glycine-conjugated chenodeoxycholic acid exhibit significantly reduced bacterial viability.

SUMMARY OF THE INVENTION

According to an aspect of some embodiments of the present invention there is provided a method of inhibiting bacterial conjugation, the method comprising contacting bacteria with an effective amount of a bile acid or a bile salt, wherein the effective amount does not affect viability of the bacteria, thereby inhibiting the bacterial conjugation.

According to an aspect of some embodiments of the present invention there is provided a method of inhibiting bacterial horizontal gene transfer, the method comprising contacting bacteria with an effective amount of a bile acid or a bile salt, wherein the effective amount does not affect viability of the bacteria, thereby inhibiting the bacterial horizontal gene transfer.

According to an aspect of some embodiments of the present invention there is provided a method of inhibiting bacterial growth, the method comprising contacting bacteria with an effective amount of a bile acid or a bile salt, wherein the effective amount does not affect viability of the bacteria, thereby inhibiting the bacterial growth.

According to an aspect of some embodiments of the present invention there is provided a method of increasing susceptibility of bacteria to antibiotic treatment, the method comprising contacting bacteria with an effective amount of a bile acid or a bile salt, wherein the bacteria are resistant to the bile acid or the bile salt, thereby increasing susceptibility of the bacteria to the antibiotic treatment.

According to an aspect of some embodiments of the present invention there is provided an article of manufacture comprising an antimicrobial agent packed separately from a bile acid or a bile salt.

According to an aspect of some embodiments of the present invention there is provided an article of manufacture comprising a disinfectant packed separately from a bile acid or a bile salt.

According to an aspect of some embodiments of the present invention there is provided a composition comprising a disinfectant and a bile acid or a bile salt.

According to an aspect of some embodiments of the present invention there is provided a composition comprising an antimicrobial agent and a bile acid or a bile salt.

According to an aspect of some embodiments of the present invention there is provided a method of inhibiting adhesion of bacteria to a surface, the method comprising applying the composition of some embodiments of the invention to a surface having the bacteria.

According to an aspect of some embodiments of the present invention there is provided a method of inhibiting biofilm formation, the method comprising applying the composition of some embodiments of the invention to a surface having the biofilm.

According to an aspect of some embodiments of the present invention there is provided a method of decontaminating a farm animal housing, the method comprising applying the composition of some embodiments of the invention to a surface in the farm animal housing.

According to an aspect of some embodiments of the present invention there is provided a method of decontaminating a medical surface having biofilm, the method comprising applying the composition of some embodiments of the invention to the medical surface having the biofilm.

According to an aspect of some embodiments of the present invention there is provided a method of treating water having biofilm, the method comprising applying the composition of some embodiments of the invention to the water having the biofilm.

According to an aspect of some embodiments of the present invention there is provided a method of assaying a decrease in conjugation frequency of bacteria, the method comprising: (a) contacting a bacteria resistant to bile acid or bile salt with a bile acid or bile salt; (b) incubating the bacteria of step (a) with other bacteria; and (c) measuring conjugation frequency between the bacteria of step (a) and the other bacteria, wherein a decrease in conjugation frequency is determined when a lower conjugation frequency is measured as compared to a conjugation frequency in the absence of the bile acid.

According to some embodiments of the invention, the bacteria are resistant to bile acid or bile salt.

According to some embodiments of the invention, the effective amount does not affect viability of the bacteria.

According to some embodiments of the invention, the effective amount inhibits bacterial conjugation.

According to some embodiments of the invention, the effective amount inhibits bacterial horizontal gene transfer.

According to some embodiments of the invention, the effective amount inhibits bacterial growth.

According to some embodiments of the invention, the bacteria are resistant to antibiotics.

According to some embodiments of the invention, the bacteria are gram negative bacteria.

According to some embodiments of the invention, the bacteria are enteropathogenic bacteria.

According to some embodiments of the invention, the bacteria are commensal or pathogenic bacteria to humans or animals.

According to some embodiments of the invention, the bacteria are selected from the group consisting of *Salmonella, Escherichia coli, Yersinia pestis, Klebsiella, Shigella, Clostridium difficile, Enterococcus faecalis, Helicobacter, Listeria monocytogenes* and *Campylobacter*.

According to some embodiments of the invention, the antimicrobial agent is an antibiotic.

According to some embodiments of the invention, the disinfectant is selected from the group consisting of a phenolic compound, an iodine or iodophor, a chlorine, a quaternary ammonium compound, an oxidizing compound and an alcohol-based disinfectant.

According to some embodiments of the invention, the bile acid is selected from the group consisting of a cholic acid, a lithocholic acid, a chenodeoxycholic acid, a deoxycholic acid, a taurine, and a derivative thereof.

According to some embodiments of the invention, the bile salt comprises an amino acid conjugated bile acid.

According to some embodiments of the invention, the article of manufacture or composition comprises a taurine conjugated bile acid or a glycine conjugated bile acid.

According to some embodiments of the invention, the composition is formulated as a liquid, a spray a gel or a powder.

According to some embodiments of the invention, the composition of some embodiments of the invention is for use in inhibiting bacterial conjugation.

According to some embodiments of the invention, the composition of some embodiments of the invention is for use in increasing susceptibility of bacteria to antibiotic treatment.

According to some embodiments of the invention, the farm animal is selected from the group consisting of a chicken, a turkey, a cow, a pig, a horse, a sheep and a goat.

According to some embodiments of the invention, the farm animal is an animal grown for the food industry.

According to some embodiments of the invention, the surface comprises at least one of a cage, a crate, a floor, a wall, a ceiling, a shelf, a fabric, a milking device or a laying surface.

According to some embodiments of the invention, the medical surface is selected from the group consisting of an endoscope, a catheter, a filter, a surgical staple, a pacemaker, a stent and an implantable device.

According to some embodiments of the invention, the surface comprises bacteria resistant to the bile acid or the bile salt.

According to some embodiments of the invention, the water is selected from the group consisting of waste water, pool water, drinking water, fresh water, seawater, and brine.

According to some embodiments of the invention, the waste water is in a sewage treatment plant.

According to some embodiments of the invention, the other bacteria comprise bacteria of the same or different species with respect to the bacteria resistant to the bile acid or the bile salt.

According to some embodiments of the invention, the bacteria are resistant to antibiotics.

According to some embodiments of the invention, the bile acid is selected from the group consisting of a cholic acid, a lithocholic acid, a chenodeoxycholic acid, a deoxycholic acid, a taurine, and a derivative thereof.

According to some embodiments of the invention, the bile salt comprises an amino acid conjugated bile acid.

According to some embodiments of the invention, the amino acid conjugated bile acid comprises a taurine conjugated bile acid or a glycine conjugated bile acid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
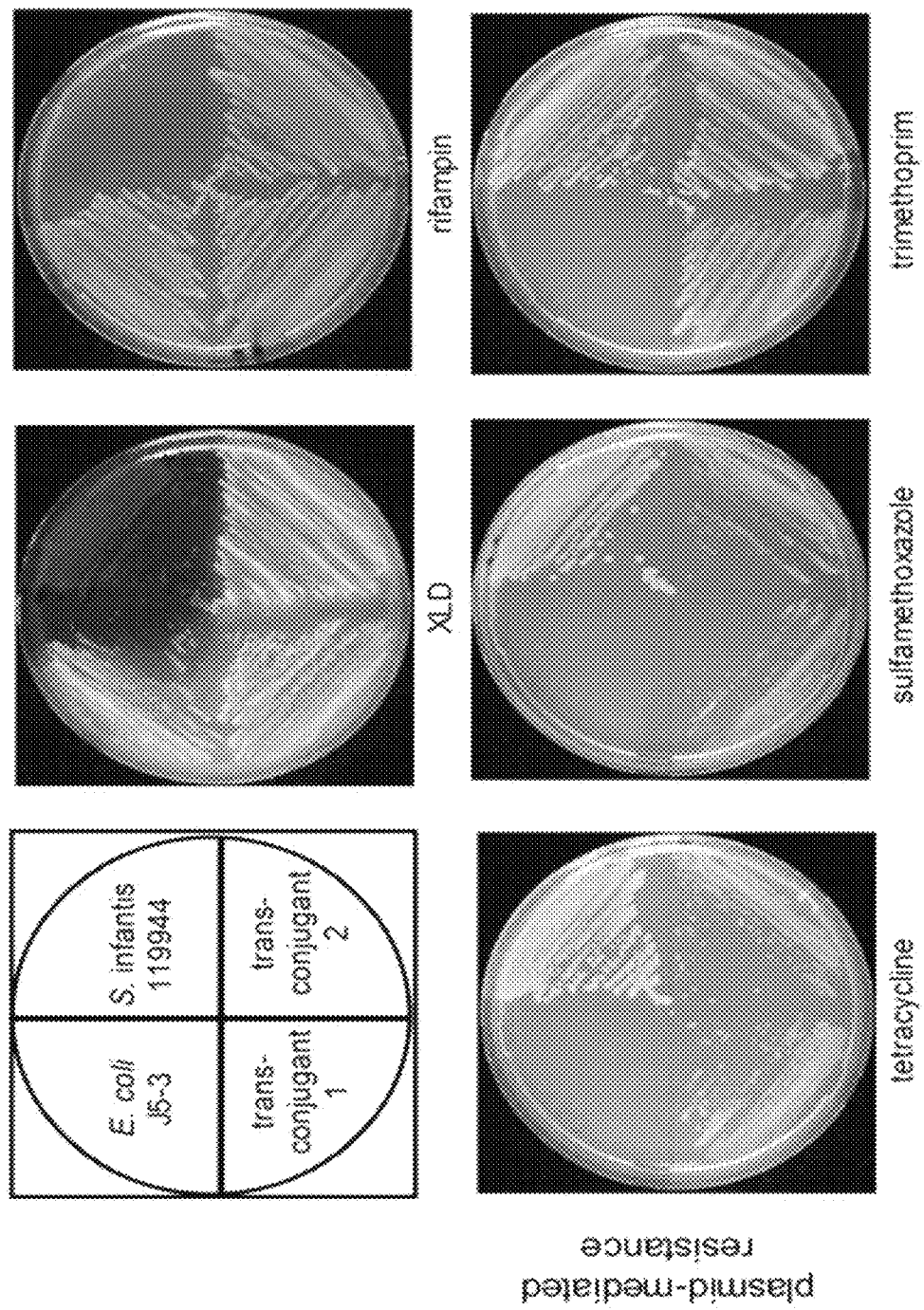

FIG. 1 depicts that the plasmid pESI confers multidrug resistance (MDR) phenotype to tetracycline, sulfamethoxazole and trimethoprim. Mating experiments between a plasmidless E. coli J5-3 strain and S. Infantis 119944 strain. Bacterial growth of the donor (S. Infantis 119944), recipient (E. coli J5-3 rifampin-resistant) and two randomly selected transconjugant isolates grown on LB plates under different selections is shown. Xylose lysine deoxycholate (XLD) was used to distinguish between the salmonella donor (appears as black colonies) and E. coli (appears as yellow colonies). The recipient strain E. coli J5-3 harbor chromosomal resistance to rifampin and therefore, transconjugants that acquired the plasmid will turn resistant to rifampin, and the other three antibiotics (tetracycline, sulfamethoxazole and trimethoprim encoded on the plasmid).

Figure 2:
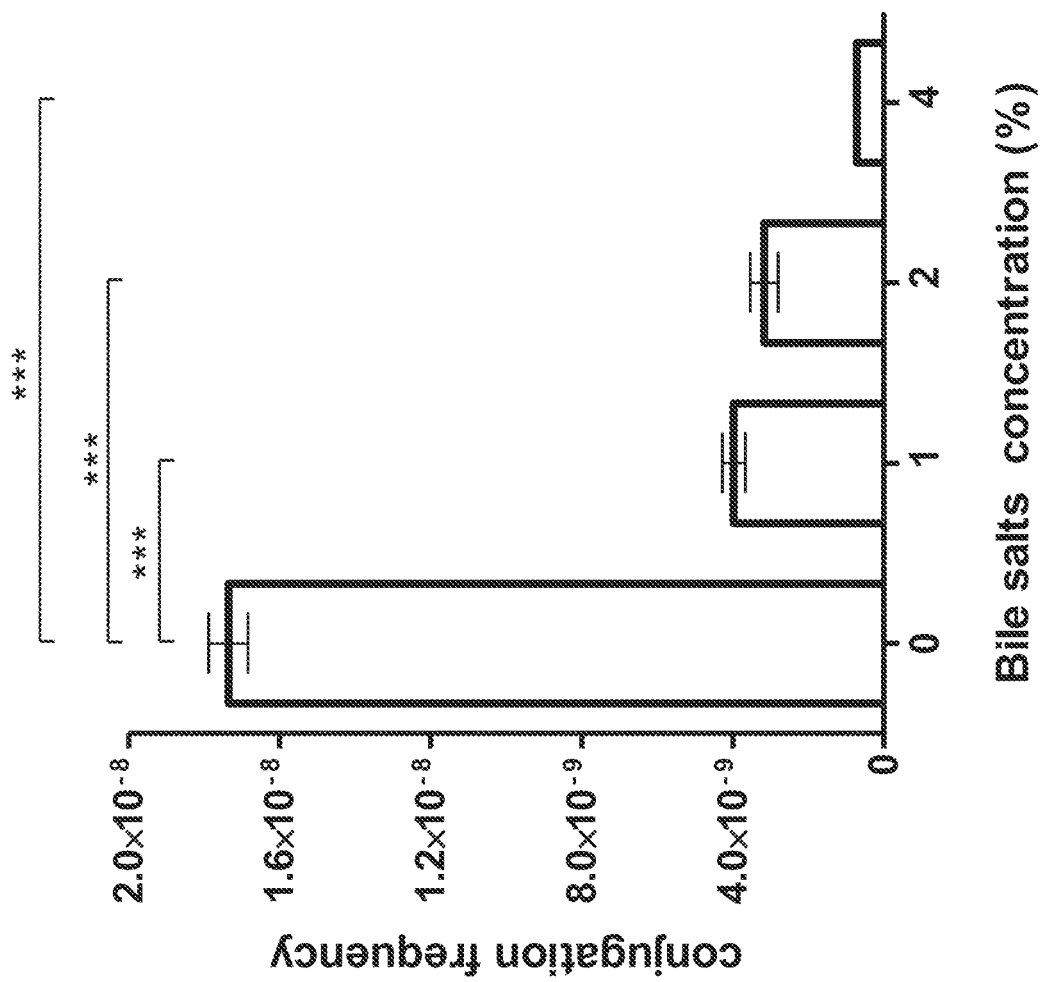

FIG. 2 is a graph depicting that pESI conjugation is repressed by bile. Conjugation frequency (obtained transconjugants/donor colony forming units [CFU]) between S. Infantis 119944 (donor) and E. coli ORN172 (recipient) was determined under increasing concentrations of bile salts. Bars show the mean and the standard error of the mean (SEM) of four independent mating experiments. One-way analysis of variance (ANOVA) with Dunnett's Multiple Comparison Test was implemented to determine statistical significance. , $P<0.001$; *, $P<0.0001$.

Figure 3:
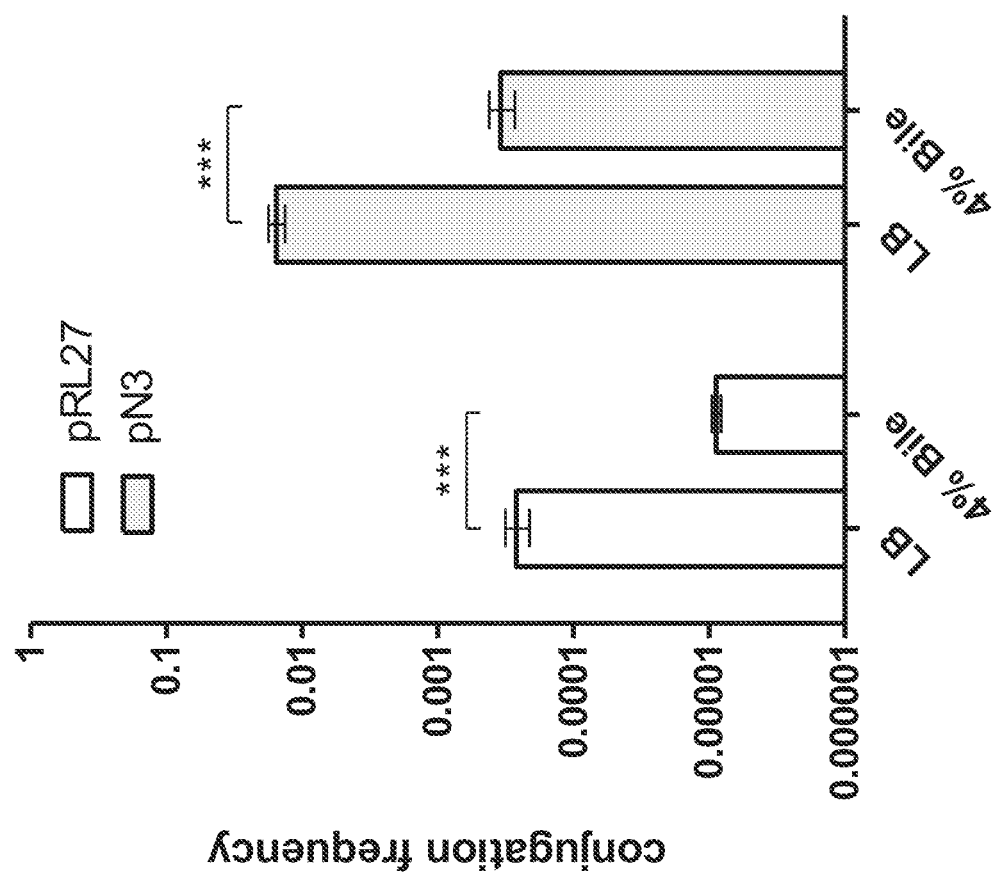

FIG. 3 is a graph depicting that bacterial conjugation is repressed by bile. Conjugation frequency (obtained transconjugants/donor CFU) between E. coli harboring pRL27 and pN3 (donor) and E. coli J5-3 (recipient) was determined in LB and in the presence of 4% bile salts. Bars show the mean and the standard error of the mean (SEM) of four independent mating experiments.

Figure 4:
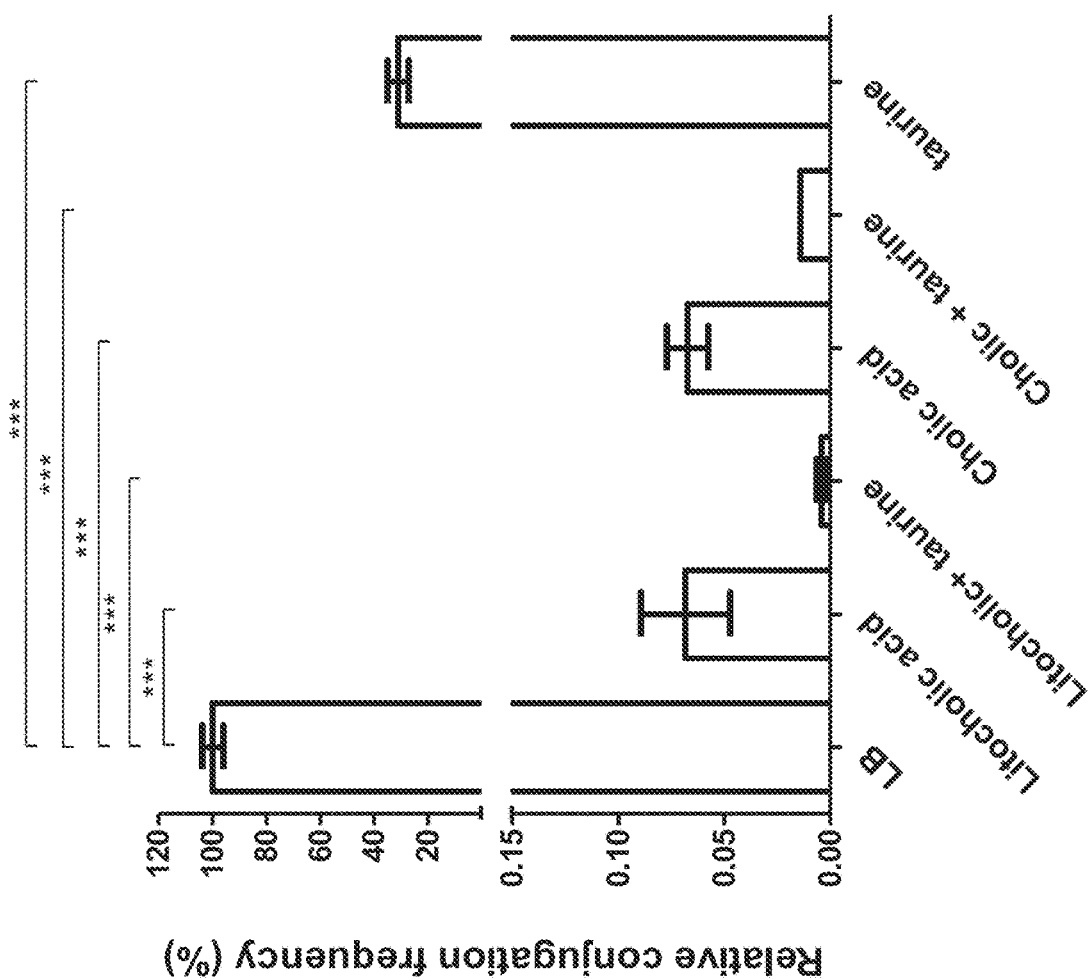

FIG. 4 is a graph depicting that compositions of 2% cholic acid and lithocholic acid without and with taurine significantly reduce bacterial conjugation. Conjugation frequency between S. Infantis 119944 and E. coli ORN172 was determined on LB agar plates supplemented with 2% (w/v) of taurine, lithocholic acid, cholic acid, lithocholic acid+taurine, and cholic+taurine. Bars show the mean and the SEM of four independent mating experiments. Of note, a composition of 2% lithocholic acid and taurine prevents bacterial conjugation.

Figure 5:
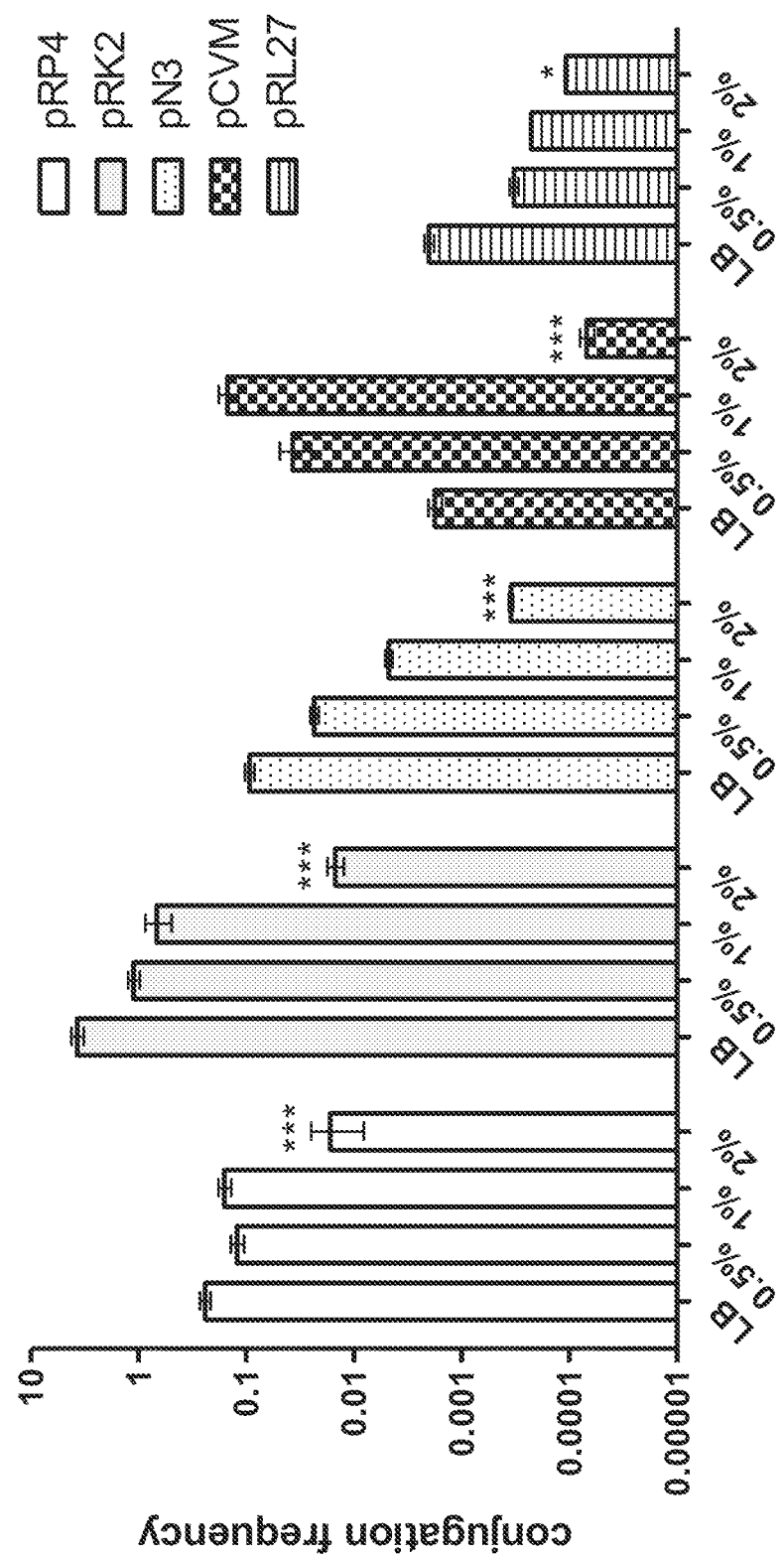

FIG. 5 is a graph depicting that bacterial conjugation is repressed by a composition of taurine and litocholic acid. Conjugation frequency between E. coli harboring pRP4, pRK2, pN3, pCVM and pRL27 (donor) and E. coli J5-3 or ORN172 (recipient) was determined in LB and in the presence of a composition comprising 0.5, 1 or 2% taurine and litocholic acid.

DESCRIPTION OF SPECIFIC EMBODIMENTS OF THE INVENTION

The present invention, in some embodiments thereof, relates to bile acids and bile salts or compositions comprising same and, more particularly, but not exclusively, to the use of same for inhibition of bacterial conjugation or bacterial horizontal gene transfer, and further for disruption of acquisition of antibiotic resistance.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The shortage of new antimicrobial drugs and the rapid spread of antimicrobial resistance between bacterial pathogens lead to the evolution of multi-resistant strains, which puts increasing pressure on the health care system. Although the market for antibacterial drugs is greater than 25 billion U.S. dollars per year, pharmaceutical companies have dramatically reduced their drug discovery programs, resulting in severe public health consequences and lack of suitable antibiotic therapy [Perry J A, et al. (2014) supra].

Thus, antimicrobial resistance of bacteria is a major challenge in modern medicine. Several bacterial mechanisms have evolved in order to acquire resistance. These include modification of existing genetic material and acquisition of new genetic material from another source. The main mechanism is the acquisition of antimicrobial resistance (AMR) genes by bacterial conjugation via plasmid transfer. Conjugation involves transfer of genetic material (e.g. DNA) via sexual pilus and requires cell to cell contact. Accordingly, DNA fragments that contain AMR genes from resistant bacterial donors can be transferred to susceptible bacteria and make previously vulnerable bacteria express resistance as coded by these newly acquired AMR genes. Therefore, the search for specific conjugation inhibitors is of special interest in the fight against superbugs and the emergence of multi drugs resistant bacteria.

While reducing the present invention to practice, the present inventors have surprisingly uncovered that bile acids and bile salts can be used to inhibit conjugation of bacteria. Specifically, the present inventors have uncovered that conjugation frequency, but not bacterial viability, between *Salmonella enterica* (e.g. S. Infantis 119944) and *E. coli* (e.g. *E. coli* ORN172) was dramatically inhibited by bile in a dose-dependent manner (FIG. 2). Furthermore, the present inventors discovered that cholic acid as well as lithocholic acid caused a significant decrease in the conjugation frequency (FIG. 4). Moreover, the addition of taurine to these bile acids, and especially to lithocholic acid, caused a further decrease in conjugation frequency bringing the conjugation frequency to almost zero (FIG. 4). Importantly, the inhibitory effect of bile on bacterial conjunction frequency was not limited to pESI (FIG. 2) and was also demonstrated for pRL27 and pN3 (FIG. 3), as well as for pRP4, pRK2, pN3, pCVM and pRL27 (FIG. 5). Taken together, the present inventors discovered a novel composition that can interfere with the bacterial conjugation process and with bacterial horizontal gene transfer and can thus be used to diminish the spread of AMR genes between bacteria. This composition may be beneficial in prevention and therapeutic applications in venues including clinics, hospitals, food and agriculture infrastructures (including animal farms), as well as in water settings such as sewage treatment plants, to fight the spread of resistant bacteria and other pathogens.

Thus, according to one aspect of the present invention there is provided a method of inhibiting bacterial conjugation, the method comprising contacting bacteria with an effective amount of a bile acid or a bile salt, wherein the effective amount does not affect viability of the bacteria, thereby inhibiting the bacterial conjugation.

According to another aspect, there is provided a method of inhibiting bacterial horizontal gene transfer, the method comprising contacting bacteria with an effective amount of a bile acid or a bile salt, wherein the effective amount does not affect viability of the bacteria, thereby inhibiting the bacterial horizontal gene transfer.

According to another aspect, there is provided a method of inhibiting bacterial growth, the method comprising contacting bacteria with an effective amount of a bile acid or a bile salt, wherein the effective amount does not affect viability of the bacteria, thereby inhibiting the bacterial growth.

According to one embodiment, the term "bile acid" refers to any natural bile acid (e.g. animal-derived bile acid or microbial-derived bile acid), chemically synthesized bile acid, bile acid prepared using phytosterol or microbial starting materials, or derivatives thereof. Exemplary bile acids include, but are not limited to, cholic acid, chenodeoxycholic acid, ursodeoxycholic acid, deoxycholic acid, lithocholic acid, hyodeoxycholic acid, glycocholic acid, taurocholic acid, 7-alpha-dehydroxylate chenodeoxycholic acid, dihydroxytaurin acid, and trihydroxytaurine acid.

According to one embodiment, the bile acid comprises a lithocholic acid.

According to one embodiment, the bile acid comprises a cholic acid.

According to one embodiment, the bile acid comprises a taurine.

The term "bile salt" refers to salts of bile acids as well as conjugated derivatives of bile acids.

According to one embodiment, the bile salt includes a cation selected from the group consisting of sodium ($Na^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH4^+$).

The terms "conjugated" or "conjugation" refers to chemical conjugation (and is in distinction to the process of biological conjugation described below) to the formation of a covalent bond. Conjugation of a bile acid is catalyzed by an enzymatic reaction that converts the bile acid to an acyl-CoA thioester then transfers the bile acid moiety from the acyl-CoA thioester to either glycine or taurine to form the respective bile acid conjugate. These additions substantially increase the acidity of the molecules and their solubility in water.

According to one embodiment, the term bile salt includes bile acids (e.g. cholic acid, chenodeoxycholic acid, deoxycholic acid, lithocholic acid, taurocholic acid, glycocholic acid) conjugated to an amino acid (e.g., glycine or taurine).

Exemplary bile salts include, but are not limited to, cholate, deoxycholate, lithocholate, chenodeoxycholate, hyodeoxycholate, glycocholate, and taurocholate.

According to one embodiment, a bile salt includes cholic acid conjugated with either glycine or taurine: glycocholate and taurocholate, respectively, or a derivative thereof.

According to one embodiment, a bile salt includes lithocholic acid conjugated with either glycine or taurine: glycine lithocholic acid and taurine lithocholic acid, respectively, or a derivative thereof.

Each possibility represents a separate embodiment of the invention.

Synthesis of bile acids or salts thereof can be carried out using any method known in the art, such as those disclosed in European Patent No. EP 2407475 and U.S. Pat. No. 5,079,240, both fully incorporated herein by reference.

It will be appreciated that any reference to a bile acid used herein includes reference to an identical compound naturally or synthetically prepared.

Furthermore, any reference to a "bile acid" or "bile salt" as used herein includes reference to one bile acid/salt, or a mixture of two bile acids/salts, three bile acids/salts, four bile acids/salts or more (i.e. at least one bile acid or salt). Furthermore, it is to be understood that any plural reference to "bile acids" or "bile salts" as used herein includes reference to one or more of such components.

As used herein, the terms "effective amount" refers to a dosage sufficient to inhibit bacterial conjugation, bacterial gene transfer or bacterial growth. This can vary depending on the type of targeted bacteria and the surface on which the bacteria reside. An effective amount can be determined by one of skill in the art especially in view of the disclosure provided below.

According to one embodiment, the effective amount does not affect viability (i.e. ability to live) of the bacteria. Bacterial viability can be determined using any method known in the art, such as but not limited to, cell viability staining and BacLight™ (as discussed in Stiefel P et al., BMC Microbiol. (2015) 15: 36, incorporated herein by reference).

According to one embodiment, the effective amount is nontoxic. Thus, according to a specific embodiment, the bile acid or bile salt (or composition comprising same as discussed hereinbelow) of the invention is provided in an effective amount which is not harmful or poisonous (e.g. does not cause death of an organism). Determination of an agent being nontoxic can be carried out following the regulations of FDA Food Code 2009: Annex 3—Public Health Reasons/Administrative Guidelines—Chapter 7, Poisonous or Toxic Materials.

The term "bacterial growth" as used herein refers to an increase in number or an increase in bacterial mass over a predetermined period of time.

According to a specific embodiment, inhibiting bacterial growth according to the present methods relates to growth of bacteria which is resistant to bile acids and/or is a drug resistant variant (e.g. resistant to antibiotics as discussed in detail hereinbelow).

The term "bacterial conjugation" as used herein refers to the direct transfer of genetic material between at least two bacterial cells (also referred to as biological conjugation as opposed to the chemical conjugation described above). Typically bacterial conjugation requires cell-to-cell contact. The bacteria may be of the same specie or of different species.

According to one embodiment, the bacterial conjugation enables transfer of genetic material from cell-to-cell (e.g. via plasmid or Integrative and Conjugative Element (ICE)), as well as of additional bacterial factors e.g. small molecules such as cytoplasmic proteins.

The term "bacterial horizontal gene transfer" as used herein refers to the direct transfer of genetic material between at least two bacterial cells, wherein the gene transfer is not via vertical transmission (i.e. is not the transmission of DNA from a parent to its offspring). Horizontal gene transfer is typically effected by cell-to-cell contact (e.g. by bacterial conjugation). However, horizontal gene transfer may not involve cell-to-cell contact and may be affected by transformation or by transduction.

Typically, transfer of genetic material (e.g. DNA) between bacteria is by direct cell-to-cell contact or by a bridge-like connection between two bacterial cells. In general, a pilus structure of the donor cell attaches to a recipient cell bringing the two cells together and enabling transfer of genetic (e.g. a plasmid or ICE) material from the donor cell to a recipient cell. Once a bacterial cell acquires the genetic material it becomes a viable donor and may transfer the genetic material to other recipient cells. The genetic material transferred is usually beneficial to the recipient bacteria, such a benefit may include, for example, antibiotic resistance, xenobiotic tolerance or the ability to use new metabolites. Conjugation is the central route by which antibiotic resistance genes and other virulence factors are propagated in bacteria. This leads to the development of multi-drug resistant variants and to the pathogenicity of previously innocuous strains.

As mentioned, transfer of genetic material (e.g. DNA) between bacteria may be affected by transformation in which the genetic material passes through the intervening medium and is taken up by the recipient bacteria. Alternatively, transfer of genetic material (e.g. DNA) between bacteria may be effected by transduction in which foreign DNA is injected into the recipient bacteria, e.g. by a bacteriophage virus.

As used herein, the term "inhibiting" refers to preventing, arresting or reducing the occurrence of bacterial conjugation, bacterial horizontal gene transfer or bacterial growth.

According to one embodiment, inhibiting bacterial conjugation is by at least about 10%, 20%, 30%, 40%, 50%, 60%, 70%, 80%, 90% or by 100% as compared to bacteria not treated by the bile acid or bile salt of the invention.

Those of skill in the art will understand that various methodologies and assays can be used to assess inhibition of bacterial conjugation.

According to one embodiment, assessing inhibition of bacterial conjugation is carried out by assessing the conjugation frequency, e.g. by calculating the ratio between the obtained transconjugant CFU and the number of bacterial donors that were used in the conjugation assay (as described in further detail below and in the Examples section which follows).

According to one embodiment, inhibiting bacterial horizontal gene transfer is by at least about 10%, 20%, 30%, 40%, 50%, 60%, 70%, 80%, 90% or by 100% as compared to bacteria not treated by the bile acid or bile salt of the invention. Those of skill in the art will understand that various methodologies and assays can be used to assess inhibition of bacterial horizontal gene transfer.

According to one embodiment, assessing inhibition of bacterial horizontal gene transfer is carried out by, e.g. PCR, southern blot, sequence composition methods or by homology methods. Additional methods are taught in Măndoiu et al., ISBRA 2008, LNBI 4983, p. 26-37, 2008, incorporated herein by reference.

According to one embodiment, inhibiting bacterial growth is by at least about 10%, 20%, 30%, 40%, 50%, 60%, 70%, 80%, 90% or by 100% as compared to bacteria not treated by the bile acid or bile salt of the invention. Those of skill in the art will understand that various methodologies and assays can be used to assess inhibition of bacterial growth.

According to one embodiment, assessing inhibition of bacterial growth is carried out e.g. by directly counting the number of cells, cell mass or colony numbers (e.g. using a microscope, flow cytometry), or by measuring the turbidity or nutrient uptake.

According to one embodiment, inhibiting bacterial conjugation or horizontal gene transfer blocks genetic transfer between bacteria including transfer of, for example, antibiotic resistant genes (e.g. tetA, ampC), adhesion factors (e.g. fimbria clusters), invasion factors (e.g. Type 3 secretion system), toxins (e.g. stx), metabolic genes (e.g. mal genes used for maltose metabolism), virulence factors (e.g. ybt), and tolerance to environmental stresses genes (e.g. mer genes).

According to one embodiment, inhibiting bacterial conjugation or horizontal gene transfer blocks genetic transfer between bacteria including acquisition of antibiotic resistance genes [e.g. those coding for multidrug resistance (MDR) to e.g. chloramphenicol acetyltransferase (CAT); β-lactamases (bla, TEM, CTX-M-3); tetracycline (tetA), sulfamethoxazole (sulI); trimethoprim (dfrA), hydrogen peroxidase (qacEΔ1), mercury (mer), etc.].

According to one embodiment, inhibiting bacterial conjugation blocks genetic transfer between bacteria including transfer of plasmids. Exemplary plasmids which transfer genetic material (e.g. antibiotic resistance genes (ARGs)) between bacteria include, but are not limited to, pESI, pRL27, pN3, pRP4, pRK2, pN3, pCVM and pRL27.

The term "bacteria" as used herein generally refers to a genus of prokaryotic microorganisms scientifically classified as such. Most bacteria can be classified as Gram-positive bacteria or Gram-negative bacteria.

Gram-positive bacteria relate to bacteria bounded by only a single unit lipid membrane and contain a thick layer (20-80 nm) of peptidoglycan, which retains the crystal violet stain in a Gram staining technique. Exemplary Gram-positive bacteria include, but are not limited to, *Actinomyces israelii*,

*Bacillus* species, *Bacillus antracis*, *Clostridium*, *Clostridium perfringens*, *Clostridium tetani*, *Cornyebacterium*, *Corynebacterium diphtheriae*, *Enterococcus*, *Erysipelothrix rhusiopathiae*, *Lactobacillus*, *Listeria*, *Mycobacterium*, *Staphylococcus*, and *Streptococcus*.

Gram-negative bacteria relate to bacteria bounded by a cytoplasmic membrane as well as an outer cell membrane, containing only a thin layer of peptidoglycan between the two membranes, which is unable to retain crystal violet stain in a Gram staining technique. Exemplary Gram-negative bacteria include, but are not limited to, *Aerobacter, Aeromonas, Acinetobacter, Agrobacterium, Bacteroides, Bartonella, Bordetella, Borrelia, Brucella, Burkholderia, Campylobacter, Calymmatobacterium, Campylobacter, Citrobacter, Chlamydia, Chlamydophila, Enterobacter, Enterobacter aerogenes, Escherichia, Francisella, Fusobacterium, Fusobacterium nucleatum, Gardnerella, Haemophilus, Hafnia, Helicobacter, Klebsiella, Klebsiella pneumoniae, Legionella, Leptospira, Morganella, Moraxella, Neisseria, Pasteurella, Pasteurella multocida, Plesiomonas, Prevotella, Proteus, Providencia, Pseudomonas, Porphyromonas, Rickettsia, Salmonella, Serratia, Shigella, Stentorophomonas, Streptobacillus, Streptobacillus moniliformis, Treponema, Treponema pallidium, Treponema pertenue, Xanthomonas, Veillonella, Vibrio*, and *Yersinia*.

According to one embodiment, the bacteria are resistant to bile acids or bile salts (i.e. are not killed by bile acids or salts, typically such bacteria acquire bile resistant genes). Typically, bacteria which reside in the gastrointestinal track (e.g. in the gallbladder, bile ducts, small intestine, large intestine and liver), where bile concentrations are high, exhibit resistance to bile acids/salts.

According to one embodiment, the bacteria are enteric bacteria (i.e. bacteria typically found in the gut of animals). Exemplary enteric bacteria include, but are not limited to, *Salmonella, Shigella, Vibrio, Campylobacter Proteus, Serratia, Enterobacter, Citrobacter, Pseudomonas, Klebsiella, Bacteroides, Clostridium, Fusobacterium, Eubacterium, Ruminococcus, Peptidococcus, Peptostreptococcus, Eschericia*, and *Bifidobacterium*.

Bacteria according to the present invention may include commensal bacteria or pathogenic bacteria that cause infections in humans or in animals, both of which may acquire antibiotic resistance.

According to one embodiment, the bacteria are pathogenic bacteria.

According to another embodiment, the bacteria are enteropathogenic bacteria. Exemplary enteropathogenic bacteria include, but are not limited to, *Salmonella enterica* (e.g. *S. Typhi* and *S. Typhimurium*), *Shigella* (*S. flexneri* and *S. dysenteriae*), *Vibrio cholerae/parahaemolyticus*, *Escherichia* (e.g. *E. coli*, e.g. *E. coli* 0157:H7), *Campylobacter jejuni, Enterococcus faecalis, Listeria monocytogenes, Klebsiella* spp., *Proteos* spp., *Clostridium difficile, Bacillus cereus* and *Helicobacter pylori*.

According to one embodiment, the bacteria are resistant to an antimicrobial treatment, such as to an antibiotics. Exemplary antibiotics include, but are not limited to, penicillin, ampicillin, tetracycline, chloramphenicol, minocycline, doxycycline, vancomycin, bacitracin, kanamycin, neomycin, gentamycin, erythromycin, spectinomycin, zeomycin, streptomycin, fluoroquinolones and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftrizoxime, ceftriaxone, cefoperazone.

According to another embodiment, the bacteria are resistant to multiple antimicrobial treatments (i.e. multidrug resistant (MDR)).

By inhibiting bacterial conjugation and/or horizontal gene transfer, the bile acid or bile salt of some embodiments of the invention can be used to reduce the spread of antibiotic resistance genes and virulence factors between bacteria by e.g. conjugation, and accordingly increase susceptibility of bacteria to treatment.

Thus, according to another aspect of the invention there is provided a method of increasing susceptibility of bacteria to antibiotic treatment, the method comprising contacting bacteria with an effective amount of a bile acid or a bile salt, wherein the bacteria are resistant to the bile acid or bile salt, thereby increasing susceptibility of the bacteria to the antibiotic treatment.

As used herein, the phrase "increasing susceptibility of bacteria" refers to bacteria which are more susceptible to an antibiotic treatment by at least about 10%, 20%, 30%, 40%, 50%, 60%, 70%, 80%, 90% or 100% as compared to bacteria not treated by the bile acid or bile salt of the invention.

Bacteria which are more susceptible to treatment will exhibit lower viability upon treatment with antibiotics. Methods for determining growth of bacteria are well known in the art. By way of example, growth of a target bacterial species or strain can be determined by growth in a culture, such as a liquid culture. In this regard, as the bacteria multiply and increase in number, the optical density of the liquid culture increases (due to the presence of an increasing number of bacterial cells). Thus, an increase in optical density indicates bacterial growth while a decrease in optical density indicates a decline in bacterial growth. For example, optical density (at for example at 600 nm) can be determined within the wells of a multi-well plate (e.g. a 96-well plate) using an automated plate reader.

As used herein the term "contacting" refers to the positioning of the bile acid or bile salt (or compositions comprising same as discussed hereinbelow) of the present invention such that they are in direct or indirect contact with the bacterial cells in such a way that the bile acid or bile salt is able to inhibit or prevent bacterial conjugation. Thus, the present invention contemplates applying the bile acid or bile salt of the present invention to a desirable surface (e.g. one which bacterial cells may grow) and/or directly to the bacterial cells (e.g. to a surface on which bacterial cells have been exemplified).

Contacting the bile acid or bile salt (or compositions comprising same as discussed hereinbelow) with a surface can be effected using any method known in the art including spraying, spreading, wetting, immersing, dipping, painting, or adhering. The compositions of the present invention may be attached as monolayers or multiple layers.

Contacting the bacteria with bile acid or bile salt can be effected on any surface in which bacteria propagate.

Bacteria can live and proliferate as individual cells in the environment (e.g. on surfaces) or they can grow as highly organized, multicellular communities encased in a self-produced polymeric matrix in close association with surfaces and interfaces, named biofilms. Biofilms are a major concern in many industries including the agriculture, food, pharmaceutical, medical, bio-engineering industries causing, amongst a wide range of negative effects, microbial infections.

Biofilms adhere to both living and non-living surfaces and may be heterogeneous (i.e. composed of multiple species of microorganisms) or may be composed of a single type of organism. Biofilms are very difficult to eliminate since microbes growing within are highly organized and can withstand hostile environments, such as high temperatures and antimicrobial agents (e.g., antibiotics).

In humans, biofilms are a cause of systemic infections (e.g., nosocomial infections) and are a major concern when introducing products into the body (e.g., contact lenses, central venous catheters, mechanical heart valves and pacemakers).

In agricultural settings, biofilms can lead to contamination and infection in animals (e.g. which can also be passed to humans as described below). For example, biofilms may grow on farming equipment (e.g. milking equipment and in tanks), housing areas (e.g. cages, coops, barns), feeding and watering device (e.g. watering cup or watering trough), and storage areas. Thus, biofilms may form on various materials such as, but not limited to, plastic, glass, stainless steel, metal, rubber, and others. Some of these bacteria are pathogenic to humans or animals. Furthermore, antimicrobial resistance strains of bacteria are a prominent problem. For example, in farm animals, the control of bacterial infections is imperative as bacteria (including resistant strains) may find its way into eggs, meat and milk providing contaminated food products.

As mentioned above, the main mechanism by which bacteria acquire resistance is by the acquisition of antimicrobial resistance (AMR) genes by bacterial conjugation and/or horizontal gene transfer (e.g. via plasmid transfer) and/or horizontal gene transfer.

Thus, according to another aspect of the present invention there is provided a method of inhibiting adhesion of bacteria to a surface, the method comprising applying the bile acid or bile salt (or compositions comprising same as discussed hereinbelow) of the present invention to a surface having bacteria.

According to another aspect of the present invention there is provided a method of inhibiting biofilm formation, the method comprising applying the bile acid or bile salt (or compositions comprising same as discussed hereinbelow) of the present invention to a surface having biofilm.

As used herein the phrase "inhibiting adhesion" refers to preventing, reducing or eliminating bacterial attachment to a surface (e.g. by reducing the rate of growth on a surface or by reducing the formation of biofilm).

According to one embodiment, the bile acid or bile salt (or compositions comprising same as discussed hereinbelow) of the present invention inhibits bacterial adhesion by 10%, 20%, 30%, 40%, 50%, 60%, 70%, 80%, 90% or by 100% as measured by a bacterial adhesion assays. Exemplary bacterial adhesion assays include, but are not limited to, high-throughput polystyrene microplate assay, qualitative bacteria adhesion assay and fluorescent microscopic assay for biofilm formation on glass slides. It will be appreciated that the compositions of some embodiments of the present invention also inhibit bacterial aggregation (i.e. aggregation not to a surface).

As used herein the term "biofilm" refers to a layer of microorganisms adhering to a surface (e.g. as dispersed microorganisms and/or in colonies) together with polymers that they secrete. Accordingly, the biofilm typically is made of polysaccharides and other macromolecules.

According to one embodiment, the bile acid or bile salt (or compositions comprising same as discussed hereinbelow) of the present invention inhibits biofilm formation by 10%, 20%, 30%, 40%, 50%, 60%, 70%, 80%, 90% or by 100% as compared to biofilm formation in the absence of the bile acid or bile salt of the invention. Biofilm formation can be determined e.g. by a biofilm assays. Exemplary assays which can be used include, but are not limited to, colorimetric and metabolic stains such as the dye crystal violet (CV) assay described in O'Toole, J Vis Exp. (2011) 47: 2437, incorporated herein by reference.

The term "surface" is defined herein as any surface which may be covered, at least in part, by a biofilm. The present invention contemplates inhibition of bacterial adhesion or biofilm formation to a wide variety of surfaces including, but not limited to, fabrics, fibers, foams, films, concretes, masonries, glass, metals, plastics, rubbers, polymers, combinations of same and like.

The present invention contemplates inhibition of bacterial adhesion or biofilm formation on organic surfaces, inorganic surfaces, or combinations of same.

According to one embodiment, the surface is a surface of farm animal housing susceptible to biofilm formation (as discussed below).

According to one embodiment, the surface is a surface of a medical device susceptible to biofilm formation (as discussed below).

According to one embodiment, the surface is a surface of a water treatment plant or device susceptible to biofilm formation (as discussed below).

According to one embodiment, the surface is comprised in a device that is susceptible to biofilm formation. Exemplary devices which surfaces are contemplated by the present invention include, but are not limited to, vessel hulls, automobile surfaces, air plane surfaces, membranes, filters, industrial equipment, bioreactors, fermentors, pools.

According to one embodiment, the surface does not comprise bacteria (and said treatment is effected as a preventive measure).

According to another embodiment, the surface already has bacteria attached thereto.

As mentioned, the method of the present invention is effected by applying the bile acid or bile salt (or compositions comprising same as discussed hereinbelow) of the present invention to a surface.

Applying the compositions with a surface can be effected using any method known in the art including spraying, spreading, wetting, immersing, dipping, painting, ultrasonic welding, welding, bonding or adhering. The compositions of the present invention may be attached as monolayers or multiple layers.

Thus, according to another aspect of the present invention there is provided a method of decontaminating a farm animal housing, the method comprising applying the bile acid or bile salt (or composition comprising same as described in detail hereinbelow) to a surface in the farm animal housing.

As used herein, the term "farm animal" refers to animals including, but not limited to, cattle, sheep, pigs, goats, horses, donkeys, chickens, turkeys, ducks, geese and rabbits.

According to one embodiment, the farm animal is grown for the food industry (e.g. for milk, eggs, meat).

As used herein, the term "farm animal housing" refers to any area in which the farm animal is breed, raised, transported or slaughtered. For example, a farm animal housing may include an animal feeding operation (also referred to as "factory farms"), open barns, indoor barns, crates, cages, stalls, coops and trucks (e.g. used for transportation of farm animals). Furthermore, the term "farm animal housing" includes milking areas (e.g. of cows, sheep and goats) and egg laying areas.

As used herein, the term "decontaminating" relates to the process of cleansing a surface to remove bacterial contaminants or to eliminate formation thereof (e.g. avoiding biofilm formation).

According to one embodiment, decontaminating a farm animal housing is effect such that reduction in bacterial numbers or biofilm is by at least about 10%, 20%, 30%, 40%, 50%, 60%, 70%, 80%, 90% or by 100% as compared to a farm animal housing not treated by the bile acid or bile salt of the invention. Those of skill in the art will understand that various methodologies and assays can be used to assess decontamination. For example, a sample may be collected on a sponge or a swab; the sample can be plated onto agar; plates can be incubated (e.g. aerobically at 37° C. for at least 24 hours); and colonies can be counted (e.g. using a counting grid).

According to one embodiment, the surface to be decontaminated includes at least one of a cage, a crate, a floor, a wall, a ceiling, a door, a shelf, a fabric, a milking device, a collection tank (e.g. milking tank), a feeding device or utensil (e.g. a feeding trough, a feeding cup, a watering cup or watering trough), or a laying surface.

Decontamination may be effected by a single administration of the bile acid or bile salt (or composition comprising same as described in detail hereinbelow) or by multiple administrations (e.g. two, three, four, five, six, seven, eight, nine, ten or more administrations). When multiple administrations are employed, these can be carried out on a single day or over several days, weeks, months or years (e.g. on consecutive days or over a prolonged period of time). One of skill in the art is capable of making such a decision taking into consideration the area to be treated and the type of bacterial contamination to be treated or prevented.

Decontamination may be effected by applying the bile acid or bile salt (or compositions comprising same as discussed hereinbelow) using any method known in the art including spraying, spreading, wetting, immersing, dipping, painting, or adhering. The compositions of the present invention may be attached as monolayers or multiple layers.

According to another aspect of the invention, there is provided a method of decontaminating a medical surface having a bacterial contamination or a biofilm, the method comprising applying the bile acid or bile salt (or composition comprising same as described in detail hereinbelow) to the medical surface having the bacterial contamination or biofilm.

According to one embodiment, decontaminating a medical surface is effect such that reduction in bacterial numbers or biofilm is by at least about 10%, 20%, 30%, 40%, 50%, 60%, 70%, 80%, 90% or by 100% as compared to a medical surface having bacterial contamination or biofilm not treated by the bile acid or bile salt (or composition comprising same) of the invention. Those of skill in the art will understand that various methodologies and assays can be used to assess decontamination, as discussed above.

As used herein the term "medical device" refers to any implant, instrument, apparatus, implement, machine, device or any other similar or related object (including any component or accessory), which is intended for use in the diagnosis, treatment, cure or prevention of disease or other conditions. Such medical device is intended for use in man or other animals and is anticipated to affect the structure or any function of the body. Such medical device does not achieve its primary intended purposes through chemical action and is not dependent upon being metabolized for the achievement of its primary intended purposes.

An implant refers to any object intended for placement in a human body that is not a living tissue. The implant may be temporary or permanent. An implant can be an article comprising artificial components, such as catheters or pacemakers. Implants can also include naturally derived objects that have been processed so that their living tissues have been devitalized. As an example, bone grafts that have been processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies.

The present invention therefore envisions decontaminating medical surfaces with the bile acid or bile salt (or compositions comprising same) of the present invention to prevent bacterial conjugation, reduce acquisition of antimicrobial resistance, and increase susceptibility of biofilm to an antimicrobial treatment (e.g. antibiotics), so as to reduce/eliminate any possible infection known to occur following implantation. Device-related infections usually result from the introduction of microorganisms, primarily bacteria, during the device insertion or implantation procedure, or from attachment of blood-borne organisms to the newly inserted device and their subsequent propagation on its surface. Applying (e.g. coating) the medical device with the compositions of the present invention will therefore inhibit bacterial conjugation in biofilm (i.e. of one or more microbial species), will prevent medical device related contamination, and consequently will improve the effect of antimicrobial treatment (when administered to combat infection) including, but not limited to antibiotics.

Medical surfaces that may be applied (e.g. coated) with the compositions of the invention include, but not limiting to, artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), anastomotic devices, vascular catheter ports, vascular stents, clamps, surgical staples, embolic devices, wound drain tubes, ocular lenses, dental implants, hydrocephalus shunts, pacemakers and implantable defibrillators, needleless connectors, voice prostheses, and the like.

Another possible application of the bile acid and bile salt compositions of the present invention is to apply same to surfaces found in the medical and dental environments. Such surfaces include the inner and outer aspects of various instruments and devices, whether disposable or intended for repeated uses. Such surfaces include the entire spectrum of articles adapted for medical use, including without limitation, endoscopes, scalpels, needles, scissors and other devices used in invasive surgical, therapeutic or diagnostic procedures; blood filters. Other examples will be readily apparent to practitioners in these arts.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and faceshields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

These bile acid and bile salt compositions of the invention can also be incorporated in combination with an antimicrobial agent (e.g., antibiotic agent) onto surfaces of medical devices. Such a combination will sufficiently kill bacteria and prevent device-related infections.

Additional surfaces that can be treated according to the teachings of the present invention include contact lenses.

Medical surfaces according to the present invention can also include laboratory articles including, but not limited to, microscopic slide, a culturing hood, a Petri dish or any other suitable type of tissue culture vessel or container known in the art.

According to another aspect of the present invention there is provided a method of treating water having a bacterial contamination or a biofilm, the method comprising applying the bile acid or bile salt (or composition comprising same as described in detail hereinbelow) to the water having the bacterial contamination or biofilm.

The term "treating" as used herein relates to the process of cleansing water to remove bacterial contaminants or to eliminate formation thereof (e.g. avoiding biofilm formation).

According to one embodiment, the water is selected from the group consisting of waste water, pool water, drinking water, fresh water, seawater, and brine.

According to one embodiment, the waste water is in a sewage treatment plant.

As used herein, the term "sewage treatment plant" refers to any system capable of removing contaminants from wastewater, e.g. from household sewage or agricultural sewage.

Treating the sewage treatment plant according to the present invention may be effected by applying the bile acid or bile salt (or compositions comprising same as discussed hereinbelow) using any method known in the art including spraying, spreading, wetting, immersing, dipping, painting, or adhering (as discussed below). Accordingly, the compositions of the present invention may be provided to any surface of the sewage plant including, for example, to tanks, pumps, filters, screens, which are typically used to treat the waste water. Furthermore, the bile acid or bile salt (or compositions comprising same as discussed hereinbelow) may be added directly to the waste water or sludge.

According to one embodiment, the bile acid or bile salt (or compositions comprising same as discussed hereinbelow) are used in conjunction with other disinfectants typically used in sewage treatment plant, such as but not limited to, ozone, chlorine, ultraviolet light, or sodium hypochlorite.

Likewise, the bile acid or bile salt (or compositions comprising same as discussed hereinbelow) can be used to treat pool water, drinking water, fresh water, seawater, and brine, using any method known in the art such as the ones described for sewage treatment plant, above.

According to one embodiment, treating water is effect such that reduction in bacterial numbers or biofilm is by at least about 10%, 20%, 30%, 40%, 50%, 60%, 70%, 80%, 90% or by 100% as compared to water not treated by the bile acid or bile salt (or composition comprising same) of the invention. Those of skill in the art will understand that various methodologies and assays can be used to assess water treatment, as discussed above.

The bile acid or bile salt of some embodiments of the invention can be utilized per se, or as part of a composition.

According to one embodiment, the composition comprises a bile acid or bile salt and a disinfectant.

The composition comprising the bile salt and the disinfectant can be in a single container or in separate containers: e.g., bile acid or bile salt packed separately from the disinfectant; or bile acid or bile salt and the disinfectant in a single container.

According to one embodiment, the composition comprises a bile acid or bile salt and a cleaning reagent.

The composition comprising the bile salt and the cleaning reagent can be in a single container or in separate containers: e.g., bile acid or bile salt packed separately from the cleaning reagent; or bile acid or bile salt and the cleaning reagent in a single container.

According to another embodiment, the composition comprises a bile acid or bile salt and an antimicrobial agent.

The composition comprising the bile salt and the antimicrobial agent can be in a single container or in separate containers: e.g., bile acid or bile salt packed separately from the antimicrobial agent; or bile acid or bile salt and the antimicrobial agent in a single container.

The amount of bile acid or bile salt to be used in the composition of the invention can be between 0.01-10% Weight/Volume (w/v). According to one embodiment, the amount of bile acid or bile salt to be used in the composition of the invention can be in the range of 0.01-1% w/v, 0.01-5% w/v, 0.1-5% w/v, 0.1-10% w/v, 1-5% w/v, 1-10% w/v, 5-10% w/v, or 7.5-10% w/v.

According to one embodiment, the bile acid or bile salt comprises sodium choleate (i.e. crude bile) at a concentration of 0.01-10% w/v. According to a specific embodiment, the concentration of sodium choleate in the composition is at least about 0.01%, 0.1%, 1%, 2%, 4%, 6%, 8% or 10% w/v.

According to one embodiment, the bile acid or bile salt comprises taurine at a concentration of 0.01-10% w/v. According to a specific embodiment, the concentration of taurine in the composition is at least about 0.01%, 0.1%, 1%, 2%, 4%, 6%, 8% or 10% w/v.

According to one embodiment, the bile acid or bile salt comprises lithocholic acid at a concentration of 0.01-10% w/v. According to a specific embodiment, the concentration of lithocholic acid in the composition is at least about 0.01%, 0.1%, 1%, 2%, 4%, 6%, 8% or 10% w/v.

According to one embodiment, the bile acid or bile salt comprises cholic acid at a concentration of 0.01-10% w/v. According to a specific embodiment, the concentration of cholic acid in the composition is at least about 0.01%, 0.1%, 1%, 2%, 4%, 6%, 8% or 10% w/v.

According to one embodiment, the bile acid or bile salt comprises lithocholic acid and taurine at a concentration of 0.01-10% w/v. According to a specific embodiment, the concentration of lithocholic acid and taurine in the composition is at least about 0.01%, 0.1%, 1%, 2%, 4%, 6%, 8% or 10% w/v.

According to one embodiment, the bile acid or bile salt comprises cholic acid and taurine at a concentration of 0.01-10% w/v. According to a specific embodiment, the concentration of cholic acid and taurine in the composition is at least about 0.01%, 0.1%, 1%, 2%, 4%, 6%, 8% or 10% w/v.

According to one embodiment, the bile acid or bile salt comprises glycine at a concentration of 0.01-10% w/v. According to a specific embodiment, the concentration of glycine in the composition is at least about 0.01%, 0.1%, 1%, 2%, 4%, 6%, 8% or 10% w/v.

According to one embodiment, the bile acid or bile salt comprises chenodeoxycholic acid at a concentration of 0.01-10% w/v. According to a specific embodiment, the concentration of chenodeoxycholic acid in the composition is at least about 0.01%, 0.1%, 1%, 2%, 4%, 6%, 8% or 10% w/v.

According to one embodiment, the bile acid or bile salt comprises deoxycholic acid at a concentration of 0.01-10% w/v. According to a specific embodiment, the concentration of deoxycholic acid in the composition is at least about 0.01%, 0.1%, 1%, 2%, 4%, 6%, 8% or 10% w/v.

As used herein, the term "antimicrobial agent" refers to a compound which kills microorganisms or inhibits their growth. The antimicrobial agent may include an antibacterial agent, an antifungal agent, an antiviral agent, an antiprotozoal agent, an antiparasitic agent, or a combination thereof. The antimicrobial agent may include an inorganic compound, an organic compound (e.g. small organic molecule), a protein, an antibody, a DNA, a carbohydrate, or combinations thereof.

According to one embodiment, the antimicrobial agent is an antibacterial agent such as an antibiotic. Exemplary antibiotics include, but are not limited to, penicillins (e.g., amoxicillin and amoxicillin-clavulanate), clavulanate acid, trimethoprim-sulfamethoxazole, fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, ceflbuten, and ceftriaxone), macrolides, azalides (e.g., erythromycin, clarithromycin, and azithromycin), sulfonamides, ampicillin, tetracycline, chloramphenicol, minocycline, doxycycline, vancomycin, bacitracin, kanamycin, neomycin, gentamycin, erythromycin, spectinomycin, zeomycin, streptomycin and combinations thereof.

Exemplary antifungal agents include, but are not limited to, terbinafine, clotrimazole, econazole, nystatin, selenium sulfide and ketoconazole.

Exemplary antiviral agents include, but are not limited to, acyclovir, famciclovir and valacyclovir.

As used herein, the term "disinfectant" refers to a substance that is applied to non-living objects to kill or inhibit the growth of microorganisms (e.g. bacteria) that are on the objects.

According to one embodiment, the disinfectant comprises an alcohol, a chlorine, a chlorine compound, an aldehyde, an oxidizing agent, an iodine, an iodophor, an ozone, a phenolic, a quaternary ammonium compound, or a mixture of two or more thereof.

According to a specific embodiment, the disinfectant comprises phenolic compounds (e.g., Pine-sol, One Stroke, Osyl), iodine or iodophors, (e.g., Betadine and Weladol), chlorine compounds (e.g., Clorox, generic bleach), quaternary ammonium compound (e.g., Roccal D Plus), alcohol-based compounds (e.g. Terralin), oxidizing compounds (e.g., Virkon S, Oxy-Sept 333), aldehyde compounds (e.g. Cidex®, Endosporine®), peracetic acid (PAA) compounds (e.g. Nu Cidex®, Anioxyde 1000®, Hydraseptic®, Peralkan®).

According to one embodiment, the disinfectant may comprise formaldehyde, ortho-phthalaldehyde, glutaraldehyde, silver dihydrogen citrate, polyaminopropyl biguanide, sodium bicarbonate, lactic acid, chlorine bleach, or a mixture of two or more thereof.

According to one embodiment, the disinfectant may comprise methanol, ethanol, n-propanol, 1-propanol, 2-propanol, isopropanol, or a mixture of two or more thereof.

According to one embodiment, the disinfectant may comprise a hypochlorite, chlorine dioxide, a dichloroisocyanurate, a monochloroisocyanurate, a halogenated hydantoin, or a mixture of two or more thereof.

According to one embodiment, the disinfectant may comprise sodium hypochlorite, calcium hypochlorite, sodium dichloroisocyanurate, sodium chlorite, N-chloro-4-methyl-benzenesulfonamide sodium salt, 2,4-dichorobenzyl alcohol, or a mixture of two or more thereof.

According to one embodiment, the disinfectant may comprise performic acid, potassium permanganate, potassium peroxymonosulfate, or a mixture of two or more thereof.

According to one embodiment, the disinfectant may comprise phenol, o-phenylphenol, chloroxylenol, hexachlorophene, thymol, amylmetacresol, or a mixture of two or more thereof.

According to one embodiment, the disinfectant may comprise benzalkonuim chloride, cetyltrimethyl ammonium bromide, cetylpyridinium chloride, benzethonium chloride, boric acid, Brilliant green, chlorhexidine gluconate, tincture of iodine, providone-iodine, mercurochrome, manuka honey, octenidine dihydrochloride, polyhexamethylene biguamide, balsam of Peru, or a mixture of two or more thereof.

According to one embodiment, the disinfectant may comprise peroxide, such as hydrogen peroxide, organic peroxides, peroxy acids, organic hydroperoxides, inorganic peroxides such as peroxide salts, acid peroxides, and mixtures of two or more thereof.

According to one embodiment, the disinfectant is part of a cleaning reagent.

The compositions of the invention may further comprise acetic acid, sulfuric acid, or a mixture thereof.

The compositions of some embodiments of the invention may further comprise one or more ingredients selected from the group consisting of: water, citrate buffer, citric acid, stabilizing agent, a surfactant (e.g. to provide the aqueous composition with surface active properties), a pH adjuster, one or more corrosion inhibitors (e.g. to provide corrosion inhibiting properties), and/or one or more chelators (e.g. to provide chelation capacity e.g. water softening).

According to one embodiment, the composition comprises water including, e.g. tap water, deionized water, distilled water, water purified by osmosis, or a mixture of two or more thereof.

According to one embodiment, the surfactant may comprise any compound that lowers surface tension or provides greater wettability. The surfactant may comprise one or more detergent, wetting agents, emulsifiers, foaming agents and/or dispersants. The surfactant may comprise one or more organic compounds that contain both hydrophobic groups and hydrophilic groups. The surfactant may comprise both a water insoluble component and a water soluble component. The surfactant may comprise one or more anionic, cationic, zwitterionic and/or nonionic compounds. The surfactant may comprise one or more alkanolamines, alkylarylsulfonates, amine oxides, poly(oxyalkylene)s, block copolymers comprising alkylene oxide repeat units, carboxylated alcohol ethoxylates, ethoxylated alcohols, alkyl phenols, ethoxylated alkyl phenols, ethoxylated amines, ethoxylated amides, oxiranes, ethoxylated fatty acids, ethoxylated fatty esters, ethoxylated oils, fatty esters, fatty acid amides, glycerol esters, glycol esters, sorbitan, sorbitan esters, imidazolines, lecithin, lignin, glycerides (e.g., mono-, di- and/or triglyceride), olefin sulfonates, phosphate esters, ethoxylated and/or propoxylated fatty acids and/or alcohols, sucrose esters, sulfates and/or alcohols and/or ethoxylated alcohols of fatty esters, sulfonates of dodecyl and/or tridecyl benzenes, sulfosuccinates, dodecyl and/or tridecyl benzene sulfonic acids, mixtures of two or more thereof, and the like. The surfactant may comprise ethanolamine, triethanolamine, octyldimethylamine oxide, nonylphenoxy poly (ethyleneoxy)ethanol, polyalkylene glycol, or a mixture of two or more thereof.

As mentioned above, the compositions of some embodiments of the invention may comprise an antibiotic.

The compositions of some embodiments of the invention may further comprise an antibiofilm enzyme. Exemplary antibiofilm enzymes include, but are not limited to, cellulase, beta-N-acetylgluconase, DispersinB, papain, DNase 1.

The composition of the invention may be prepared as one or more of a liquid (e.g. a disinfecting solution, a dip solution or a soak), a gel, a paste, a spray, a microcapsule, a granule or a powder (e.g. dry powder).

Accordingly, the composition may be used for coating, spraying, misting, soaking, dispersing, powdering, flushing, wiping, dipping and/or rinsing.

The composition of the invention may further comprise additional components, such as carriers, surfactants, emulsifiers, drying agents, film forming agents and combinations thereof. The types and concentrations of the additional components can be selected based on the intended formulation and use of the composition, and can be determined by one of skill in the art (see e.g. U.S. Patent Application no. 2015/366210, incorporated herein by reference). For example, if a composition is intended to be used as a powder, it may comprise a solid carrier, such as talc, clay, chalk, volcanic ash, or other inert ingredient (see e.g. U.S. Patent Application no. 2015/366210, incorporated herein by reference).

According to one embodiment, the composition may be formulated as a micro encapsulated formulation or a formulation that provides a delayed release. Micro encapsulation may be achieved with one or more film forming agents or pre-formed beads (e.g., selective release polymer beads) (see e.g. U.S. Patent Application no. 2015/366210, incorporated herein by reference).

Compositions of the present invention may, if desired, be presented in a pack or dispenser device. The pack may, for example, comprise metal or plastic foil. The pack or dispenser device may be accompanied by instructions for use. The pack or dispenser device may also be accompanied by a notice in a form prescribed by a governmental agency regulating the manufacture, use, or sale of the composition, which notice is reflective of approval by the agency of the form of the compositions for human or veterinary use. Such notice, for example, may include labeling approved by the U.S. Food and Drug Administration for drugs or of an approved product insert.

For any preparation used in the methods of the invention, the effective amount can be estimated initially from in vitro assays. For example, an effective amount can be formulated using cell cultures (e.g. in vitro bacterial cultures and assays) to achieve a desired concentration or titer. The data obtained from these in vitro and cell culture assays can be used in formulating a range of concentrations for use in decontamination. The concentrations may vary depending upon the surface to be treated and the type of bacteria. The exact formulation can be determined by one of skill in the art.

According to one embodiment, there is provided a method of assaying a decrease in conjugation frequency of bacteria, the method comprising:

(a) contacting a bacteria resistant to bile acid or bile salt with a bile acid or bile salt;

(b) incubating the bacteria of step (a) with other bacteria; and (c) measuring conjugation frequency between the bacteria of step (a); and the other bacteria, wherein a decrease in conjugation frequency is determined when a lower conjugation frequency is measured as compared to a conjugation frequency in the absence of the bile acid.

According to one embodiment, conjugation frequency is calculated as the ratio between the obtained transconjugant colony forming units (CFU) and the number of bacterial donors that were used in the conjugation assay.

A transconjugant refers to bacteria that have accepted a genetic material (e.g. plasmid DNA) from other donor bacteria via bacterial conjugation.

According to one embodiment, the other bacteria comprise bacteria of the same or different species with respect to the bacteria resistant to the bile acid or bile salt.

According to one embodiment, the other bacteria are resistant to bile acid or bile salt.

According to one embodiment, a decrease in conjugation frequency is by at least about 10%, 20%, 30%, 40%, 50%, 60%, 70%, 80%, 90% or by 100% as compared to bacteria not treated by the bile acid or bile salt of the invention.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Conditions

Mating Experiments pESI transfer by conjugation was performed using S. Infantis strain (119944) as the donor and a kanamycin resistant E. coli K-12, ORN172, as a recipient on LB agar plates for 16 hours. Conjugation was tested after both strains were grown in LB for 16 hours with aeration and 1 ml from each strain was harvested by centrifugation and was resuspended in 100 µl of LB medium. Equal amounts (10 µl; approximately 2×10$^9$ CFU) from each culture were mixed and placed onto LB agar plates supplemented with different concentrations bile. Resulting transconjugants were scraped from the plate, resuspended in LB broth and serial dilutions were plated on LB agar plates supplemented with tetracycline (to select for pESI) and kanamycin (to select for the recipient strain). Conjugation frequency was calculated as the ratio between the obtained E. coli transconjugants (tetracycline and kanamycin resistant CFU and the number of donor (S. Infantis 119944) that was used in the experiment.

All bile component reagents were purchased from Sigma-Aldrich Israel. The different formulations used:

Sodium choleate (crude bile from ox) at concentrations of 1, 2, and 4%; 2% taurine; 2% Lithocholic acid; 2% Cholic acid; 2% Lithocholic acid+taurine; 2% Cholic+taurine; 4% glycine; and 4% chenodeoxycholic acid.

Example 1

The Contribution of Conjugative Plasmids to Bacterial Resistance and Virulence

Recently, the present inventors have identified that the emergence of a multi-drug resistant *Salmonella enterica* serovar Infantis (S. Infantis) in Israel was facilitated by the acquisition of a large conjugative plasmid designated pESI [Aviv G. et al. (2014) *Environ Microbiol* 16: 977-994; Gal-Mor O. et al. (2010) *Emerg Infect Dis* 16: 1754-1757]. This Plasmid encodes for multiple chemical tolerance and antibiotic resistance genes (ARGs) conferring multidrug resistance (MDR) to tetracycline (tetA), sulfamethoxazole (sulI), trimethoprim (dfrA), hydrogen peroxidase (qacEΔ1) and mercury (mer) and encodes for several virulence factors such as unique chaperone-usher fimbria (fea and ipf) and the yersiniabactin (ybt) operon. Various experiments have demonstrated that the presence of pESI in bacteria not only confers an MDR phenotype (FIG. 1), but also enhances biofilm formation, adherence to and invasion into avian and mammalian host cells and increases the virulence of its bacterial host in-vivo [Aviv G. et al. (2014), supra]. Furthermore, the fact that the MDR S. Infantis strain has emerged in poultry before it was transmitted to humans [Gal-Mor O. et al. (2010), supra] further emphasis the potential role of the agriculture sector in the emergence of new MDR pathogens. Recent analysis that tested the presence of pESI in current S. Infantis isolates from food, clinical and poultry sources have shown that pESI was present in all (49/49) isolates tested [Aviv G et al., (2016) MBio 7], indicating that it is highly stable in this host.

Example 2

Bacterial Conjugation is Inhibited by Bile

Salmonella enterica, like many other enteric pathogens is resistant to bile. Nonetheless, when conjugation experiments were conducted in the lab between S. Infantis 119944 (donor) and E. coli ORN172 (recipient), it was found that the conjugation frequency, but not bacterial viability, was dramatically inhibited by bile. In these experiments, it was shown that the transfer of the S. Infantis plasmid, pESI is dramatically inhibited in a dose-response manner in the presence of bile (FIG. 2).

To verify the inhibitory effect of bile on bacterial conjugation and to validate that this activity is not specific to the pESI plasmid of S. Infantis only, the present inventors examined the conjugation frequency of two additional broad-host plasmids (pRL27 and pN3) from different incompatibility groups in the presence of 4% bile. Again, although bile did not compromise bacterial viability, it was found to dramatically reduce conjugation frequency of pRL27 and pN3 by 30- and 43-fold, respectively (FIG. 3).

Example 3

A Composition of Taurine and Lithocholic Acid is Highly Efficient in Inhibiting Bacterial Conjugation Exported human bile salts are the product of primary bile acids (cholic acid, chenodeoxycholic acid, deoxycholic acid and lithocholic acid) conjugated with either glycine or taurine, before being secreted from the liver. To characterize the potential of these compounds to inhibit bacterial conjugation, conjugation experiments were conducted using LB agar plates containing 2% of different bile acids, glycine, taurine and different mixtures of these compounds. These experiments showed that cholic acid as well as lithocholic acid caused a significant decrease in the conjugation frequency (FIG. 4). In addition, it was found that addition of taurine to these bile acids, and especially to lithocholic acid, caused a further decrease of the conjugation frequency close to the detection level (i.e. the conjugation frequency was almost zero) (FIG. 4). On the other hand, the presence of taurine alone was found to inhibit conjugation to a lower degree (FIG. 4). Therefore, it was concluded that a solution of 2% (w/v) of lithocholic acid (3α-hydroxy-5β-cholan-24-oic acid) and taurine (2-aminoethanesulfonic acid) is a potent compound in inhibiting bacterial conjugation. Noteworthy, lithocholic acids, as well as taurine had no effect on the growth rate of S. Infantis and the E. coli strains, indicating that its activity is specific against conjugation, without bactericidal effect. In contrast, the presence of 2% glycine and chenodeoxycholic acid inhibited the growth of these bacteria, and therefore transconjugants in the presence of these regents were not produced (data not shown).

To further confirm the inhibitory effect of litocholic acid and taurine on plasmid conjugation, the conjugation frequency of five different plasmids from diverse incompatibility groups was determined in the presence of a composition comprising 0, 0.5, 1 and 2% litocholic acid and taurine. Clearly, the conjugation frequency of all five plasmids was significantly impaired by up to 275-fold in the presence of 2% litocholic acid and taurine (FIG. 5), indicating that this compound is an efficient reagent to inhibit antibiotic resistant plasmid conjugation.

In summary, the current results illustrated that a composition comprising 2% lithocholic acid (3α-hydroxy-β5-cholan-24-oic acid) and taurine (2-aminoethanesulfonic acid) is highly efficient in inhibiting bacterial conjugation, without affecting bacterial viability. Therefore, this composition can be used as a prophylactic to reduce ARGs dissemination by bacterial conjugation. In addition, these results demonstrated that plasmid conjugation can be inhibited by bioactive small molecules and thus such approach can be useful to fight antibiotic resistance dissemination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of inhibiting bacterial conjugation or bacterial horizontal gene transfer, the method comprising contacting bacteria with an effective amount of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, and wherein when said bile acid or bile salt is comprised in a composition comprising antibiotics, said antibiotics are selected from the group consisting of penicillin, clavulanate acid, trimethoprim-sulfamethoxazole, fluoroquinolone, cephalosporin, macrolide, azalide, sulfonamide, ampicillin, tetracycline, chloramphenicol, minocycline, doxycycline, vancomycin, bacitracin, kanamycin, neomycin, gentamycin, erythromycin, spectinomycin, zeomycin and streptomycin, thereby inhibiting the bacterial conjugation or bacterial horizontal gene transfer.

2. The method of claim 1, wherein said bacteria are:
enteropathogenic bacteria; and/or
commensal or pathogenic bacteria to humans or animals.

3. The method of claim 1, wherein said bile salt comprises an amino acid conjugated bile acid.

4. The method of claim 3, comprising a taurine conjugated bile acid or a glycine conjugated bile acid.

5. A method of inhibiting bacterial conjugation or bacterial horizontal gene transfer of enteric bacteria, the method comprising contacting enteric bacteria with an effective amount of a bile acid or a bile salt, wherein said bile acid comprises lithocholic acid or glycocholic acid or salt thereof at a concentration of 1-5% (w/v), wherein said effective amount does not affect viability of said bacteria, and wherein when said bile acid or bile salt is comprised in a composition comprising antibiotics, said antibiotics are selected from the group consisting of penicillin, clavulanate acid, trimethoprim-sulfamethoxazole, fluoroquinolone, cephalosporin, macrolide, azalide, sulfonamide, ampicillin, tetracycline, chloramphenicol, minocycline, doxycycline, vancomycin, bacitracin, kanamycin, neomycin, gentamycin, erythromycin, spectinomycin, zeomycin and streptomycin, thereby inhibiting the bacterial conjugation or bacterial horizontal gene transfer of said enteric bacteria.

6. The method of claim 5, wherein said enteric bacteria are resistant to said bile acid or said bile salt.

7. The method of claim 5, wherein said enteric bacteria are:
enteropathogenic bacteria; and/or
commensal or pathogenic bacteria to humans or animals.

8. The method of claim 5, wherein said bile salt comprises an amino acid conjugated bile acid.

9. The method of claim 8, comprising a taurine conjugated bile acid or a glycine conjugated bile acid.

10. A method of inhibiting bacterial conjugation or bacterial horizontal gene transfer, the method comprising contacting bacteria with an effective amount of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, and wherein said bile acid or said bile salt is not co-formulated with an antibiotics.

11. The method of claim 10, wherein said bacteria are:
enteropathogenic bacteria; and/or
commensal or pathogenic bacteria to humans or animals.

12. The method of claim 10, wherein said bile salt comprises an amino acid conjugated bile acid.

13. The method of claim 12, comprising a taurine conjugated bile acid or a glycine conjugated bile acid.

14. A method of inhibiting bacterial conjugation or bacterial horizontal gene transfer, the method comprising contacting bacteria with an effective amount of a composition consisting of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, thereby inhibiting the bacterial conjugation or bacterial horizontal gene transfer.

15. The method of claim 14, wherein said bacteria are:
enteropathogenic bacteria; and/or
commensal or pathogenic bacteria to humans or animals.

16. The method of claim 14, wherein said bile salt comprises an amino acid conjugated bile acid.

17. The method of claim 16, comprising a taurine conjugated bile acid or a glycine conjugated bile acid.

18. A method of inhibiting bacterial conjugation or bacterial horizontal gene transfer, the method comprising contacting bacteria with an effective amount of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, and wherein said bile acid or bile salt is comprised in a composition comprising antibiotics, said antibiotics are selected from the group consisting of penicillin, clavulanate acid, trimethoprim-sulfamethoxazole, fluoroquinolone, cephalosporin, macrolide, azalide, sulfonamide, ampicillin, tetracycline, chloramphenicol, minocycline, doxycycline, vancomycin, bacitracin, kanamycin, neomycin, gentamycin, erythromycin, spectinomycin, zeomycin and streptomycin, thereby inhibiting the bacterial conjugation or bacterial horizontal gene transfer.

19. The method of claim 18, wherein said bacteria are:
enteropathogenic bacteria; and/or
commensal or pathogenic bacteria to humans or animals.

20. The method of claim 18, wherein said bile salt comprises an amino acid conjugated bile acid.

21. The method of claim 20, comprising a taurine conjugated bile acid or a glycine conjugated bile acid.

22. A method of inhibiting bacterial conjugation or bacterial horizontal gene transfer, the method comprising contacting bacteria with an effective amount of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, and wherein the method further comprises contacting said bacteria with antibiotics, said bile salt or said bile acid and said antibiotics not being co-formulated, thereby inhibiting the bacterial conjugation or bacterial horizontal gene transfer.

23. The method of claim 22, wherein said bacteria are:
enteropathogenic bacteria; and/or
commensal or pathogenic bacteria to humans or animals.

24. The method of claim 22, wherein said bile salt comprises an amino acid conjugated bile acid.

25. The method of claim 24, comprising a taurine conjugated bile acid or a glycine conjugated bile acid.

26. A method of inhibiting bacterial conjugation or bacterial horizontal gene transfer, the method comprising contacting bacteria with an effective amount of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, and wherein said contacting is by coating, spraying, misting, soaking, dispersing, powdering, flushing, wiping, dipping, rinsing, spreading, wetting, immersing, painting or adhering to a surface, thereby inhibiting the bacterial conjugation or bacterial horizontal gene transfer.

27. The method of claim 26, wherein said surface is selected from the group consisting of a fabric, a fiber, a foam, a film, a concrete, a masonry, a glass, a metal, a plastic, a rubber, a polymer, or combinations thereof.

28. A method of inhibiting bacterial conjugation or bacterial horizontal gene transfer, the method comprising contacting bacteria with an effective amount of a bile acid or a bile salt, wherein said bile acid comprises lithocholic acid or glycocholic acid or salt thereof at a concentration of 1-5% (w/v), wherein said bacteria are resistant to said bile acid or said bile salt, and wherein said effective amount does not affect viability of said bacteria, and wherein said bile acid or said bile salt is attached to a surface, thereby inhibiting the bacterial conjugation or bacterial horizontal gene transfer.

29. The method of claim 28, wherein said bile acid or said bile salt coats said surface.

30. The method of claim 28, wherein said surface is selected from the group consisting of a fabric, a fiber, a foam, a film, a concrete, a masonry, a glass, a metal, a plastic, a rubber, a polymer, or combinations thereof.

* * * * *